United States Patent
Maeji et al.

(10) Patent No.: US 10,786,606 B2
(45) Date of Patent: Sep. 29, 2020

(54) FUNCTIONAL COATING

(71) Applicant: Anteo Technologies Pty Ltd, Eight Mile Plains, QLD (AU)

(72) Inventors: Nobuyoshi Joe Maeji, Eight Mile Plains (AU); Chang-Yi Huang, Calamvale (AU)

(73) Assignee: ANTEO TECHNOLOGIES PTY LTD., Queensland (AU)

( * ) Notice: Subject to any disclaimer, the term of this patent is extended or adjusted under 35 U.S.C. 154(b) by 102 days.

(21) Appl. No.: 15/753,266

(22) PCT Filed: Aug. 19, 2016

(86) PCT No.: PCT/AU2016/050768
§ 371 (c)(1),
(2) Date: Feb. 17, 2018

(87) PCT Pub. No.: WO2017/027931
PCT Pub. Date: Feb. 23, 2017

(65) Prior Publication Data
US 2018/0243485 A1 Aug. 30, 2018

(30) Foreign Application Priority Data
Aug. 20, 2015 (AU) .................. 2015903374

(51) Int. Cl.
| | | |
|---|---|---|
| A61L 33/00 | (2006.01) | |
| A61K 47/69 | (2017.01) | |
| A61K 47/54 | (2017.01) | |
| A61K 31/727 | (2006.01) | |
| A61L 33/04 | (2006.01) | |
| A61L 33/06 | (2006.01) | |
| B82Y 30/00 | (2011.01) | |

(52) U.S. Cl.
CPC ........ *A61L 33/0017* (2013.01); *A61K 31/727* (2013.01); *A61K 47/54* (2017.08); *A61K 47/6929* (2017.08); *A61L 33/0011* (2013.01); *A61L 33/0076* (2013.01); *A61L 33/0082* (2013.01); *A61L 33/04* (2013.01); *A61L 33/068* (2013.01); *B82Y 30/00* (2013.01)

(58) Field of Classification Search
CPC .. A61K 47/6929; A61K 47/54; A61K 31/727; A61L 33/0017; A61L 33/0076; A61L 33/0011; A61L 33/0082; A61L 33/04; A61L 33/068; B82Y 30/00
See application file for complete search history.

(56) References Cited

U.S. PATENT DOCUMENTS

| | | | |
|---|---|---|---|
| 3,932,627 A | 1/1976 | Margraf | |
| 2006/0115514 A1* | 6/2006 | Gengrinovitch | ........ A61L 27/54 424/423 |
| 2008/0249298 A1 | 10/2008 | Ulmer et al. | |
| 2012/0177910 A1 | 7/2012 | Weber | |
| 2013/0184447 A1 | 7/2013 | Piccariello | |

FOREIGN PATENT DOCUMENTS

| | | |
|---|---|---|
| EP | 0437875 B1 | 3/1994 |
| WO | WO 2006/002472 A1 | 1/2006 |
| WO | WO 2006/056984 A2 | 6/2006 |
| WO | WO 2015/021509 A1 | 2/2015 |

OTHER PUBLICATIONS

Mariola Puszyńska-Tuszkanow et al., "Silver(I) complexes with hydantoins and allantoin Synthesis, crystal and molecular structure, cytotoxicity and pharmacokinetics", Journal of Inorganic Biochemistry 105 (2011) 17-22. (Year: 2011).*
International Search Report issued in International Application No. PCT/AU2016/050768, dated Nov. 14, 2016.
Written Opinion of the International Searching Authority issued in International Application No. PCT/AU2016/050768, dated Nov. 14, 2016.
International Preliminary Report on Patentability issued in International Application No. PCT/AU2016/050768, dated Feb. 20, 2018.

* cited by examiner

*Primary Examiner* — Mina Haghighatian
*Assistant Examiner* — Nathan W Schlientz
(74) *Attorney, Agent, or Firm* — Charles C. Achkar; Ostrolenk Faber LLP.

(57) ABSTRACT

The present invention relates to the coating of a range of functional heparins onto the surface of a substrate for which hemocompatibility is a key functional characteristic, such that the functionality of the functional heparin is maintained. The approach employs a metal coordination complex to bind to the substrate with the functional heparin binding to the metal coordination complex to thereby impart hemocompatibility.

18 Claims, 8 Drawing Sheets

FUNCTIONAL COATING

CROSS REFERENCE TO RELATED APPLICATIONS

The present application is a § 371 National Phase application based on PCT/AU2016/050768 filed Aug. 19, 2016, which claims the benefit of Australian application No. 2015903374 filed Aug. 20, 2015 the subject matter of each of which is incorporated by reference in their entirety.

FIELD OF THE INVENTION

The invention relates to the field of functional coatings and, in particular, hemocompatible coatings. More particularly, this invention relates to substrates such as medical devices, nanoparticles, blood containers, blood handling implements, and the like, which comprise a functional heparin coating.

BACKGROUND TO THE INVENTION

Any reference to background art herein is not to be construed as an admission that such art constitutes common general knowledge in Australia or elsewhere.

Due to the risk of blood clotting there is a need for hemocompatible substrates such as implantable medical devices, including, for example, artificial hearts, artificial cardiac valves, artificial blood vessels, blood vessel catheters, cannulas, stents and the like, to present functional antithrombotic coatings. Blood containers such as vacutainers, blood oxygenators and a wide range of blood handling products also require such a coating. Further, heparin coatings have found a range of uses when applied to nanoparticles including as cancer targeting and therapeutic agents as well as delivery vehicles for imaging agents, taking advantage of the biocompatibility of the antithrombotic coating. Finally, affinity chromatography may employ an antithrombotic coating, such as a heparin coating, as a general affinity ligand for use with plasma coagulation proteins, nucleic acid enzymes, lipases and the like.

Heparin has already been commonly used to impart anticoagulant properties to medical devices such as stents, but a systemic use of heparin may have undesirable side effects such as easy bleeding, heparin induced thrombocytopenia and other symptoms. For some applications, it maybe desirable that heparin is released such that a device has some controlled period of antithrombogenicity but for other situations, such as blood handling, affinity columns and nanoparticle delivery vehicles, it may be undesirable to have the heparin coating released into the analytical sample and/or the patient's body.

Heparin and the structurally related heparin sulphates form one family within a broad class of highly negatively charged polysaccharides, composed of repeating disaccharide units comprising uronic acids and glucosamines. Heparin is most commonly known as an anticoagulant and it exerts its effects by binding to antithrombin to thereby increase neutralisation of the coagulation cascade. However, it is also known that heparin exhibits other biological activities such as inhibiting angiogenesis in cancer treatment, contributing to wound healing, providing a highly biocompatible coating for nanoparticle delivery vehicles, and others. This being the case, it is important that its functionality is not compromised when it is bound to the surface of materials used in medical device, nanoparticles and many other diverse applications.

There are two general approaches to binding heparin and other functionally related polysaccharides to the material coating surface. The first is the covalent attachment of heparin preferentially via a linker or spacer unit to distance it from the coating surface and allow for conformational flexibility. For example, linking chemistries such as triazole or thioether formation have been used. While many medical devices are made of or have polymeric surfaces, such as polyvinylchloride (PVC), nylon, polyvinylpyrrolidone (PVP), and polyurethanes, amongst others; non-plastics such as steel, titanium oxides, and other metal or metalloid oxides are also used. These materials/surfaces to be coated do not have suitable functional groups for covalent coupling, such as hydroxyl, carboxyl, amino orthiol groups and so further modification is required. So, in these situations, not only is modification of the heparin molecule required but also the substrate surface itself. Such approaches complicate manufacture and result in the need for the development of chemistries that are often specific to the materials being used and/or spacer molecule.

The second general approach takes in non-covalent methods such as physical adsorption or ionic interactions. Such methods are either prone to displacement of the coating when exposed to blood or alternatively lead to poor or varying biological activity as a consequence of poor conformational freedom of the heparin molecule.

Further, in many applications functionally active surface bound heparin, depending on the underlying substrate, may not be sufficient to prevent coagulation as well as providing for improved biocompatibility. Coated materials also require a degree of lubricity giving non-fouling characteristics and so heparin may need to be part of a larger coating process employing other synthetic and/or biological reagents and polymers. Considering the large number of applications spanning a variety of material types as well as different shape and size applications ranging from nanoparticles to medical devices, a simple method of forming such coatings would be desirable.

Therefore, and in view of the foregoing, it is desirable to strongly bond heparin and functionally related polysaccharides, with or without other synthetic and/or biological reagents and polymers, to form antithrombotic coatings or provide any other functionality of heparin to the surfaces of various substrates including implantable medical devices, drug delivery nanoparticles, blood handling products, and the like. It is also desirable that the bonding approach is applicable to a range of substrate materials requiring such antithrombotic/hemocompatible coatings, and that the bonding be such that the heparin will remain functional with some predetermined level of stability, according to the application.

SUMMARY OF INVENTION

The present invention is predicated, at least in part, on the finding that a wide range of functional heparins, inclusive of heparin, sulphated heparins, high molecular weight heparin analogues, low molecular weight heparin analogues etc., can be simply and cost effectively coated onto the surface of a variety of substrate materials for which hemocompatibility is a key functional characteristic, such that the functionality of the functional heparin, including for example its anticoagulant activity, is maintained. The approach described, employing a metal coordination complex to bind to a substrate to impart hemocompatibility or bind to a preexisting hemocompatible substrate to bind and present the functional heparin, provides a significant degree of flexibility in the attachment and presentation of the functional heparin without the complexity of existing covalent bond formation or the poor control associated with passive or non-specific interactions.

According to a first aspect of the invention, there is provided a substrate having a hemocompatible coating comprising:

(a) a metal coordination complex bonded to a surface of the substrate; and (b) a functional heparin layer bonded directly to the metal coordination complex.

In one embodiment, the functional heparin layer is bonded directly to the metal coordination complex through one or more coordinate bonds.

In one highly preferred embodiment, the metal coordination complex is an oligomeric metal coordination complex.

In certain embodiments, the hemocompatible coating may further comprise a co-bonding agent.

A second aspect of the invention provides for a method of forming a hemocompatible coating on a substrate including the steps of:

(a) forming a metal coordination complex on a surface of the substrate;

(b) coating the metal coordination complex with a functional heparin such that the functional heparin bonds directly to the metal coordination complex layer, to thereby form the hemocompatible coating on the substrate.

A third aspect of the invention provides for a method of reducing the incidence of thrombosis in a target area of a patient including implanting the substrate with the hemocompatible coating of the first aspect within the target area.

In this embodiment, the substrate with the hemocompatible coating is preferably a medical device.

A fourth aspect of the invention resides in a kit comprising:

(a) a vial comprising a solution of a metal coordination complex; and (b) a vial comprising a functional heparin solution;

wherein the solution of the metal coordination complex is adapted to be applied to a surface of a substrate to form a layer thereon and the functional heparin solution is adapted to be applied to the metal coordination complex layer to bind thereto and form a hemocompatible coating on the substrate.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

DETAILED DESCRIPTION

Definitions

Figure 1A:
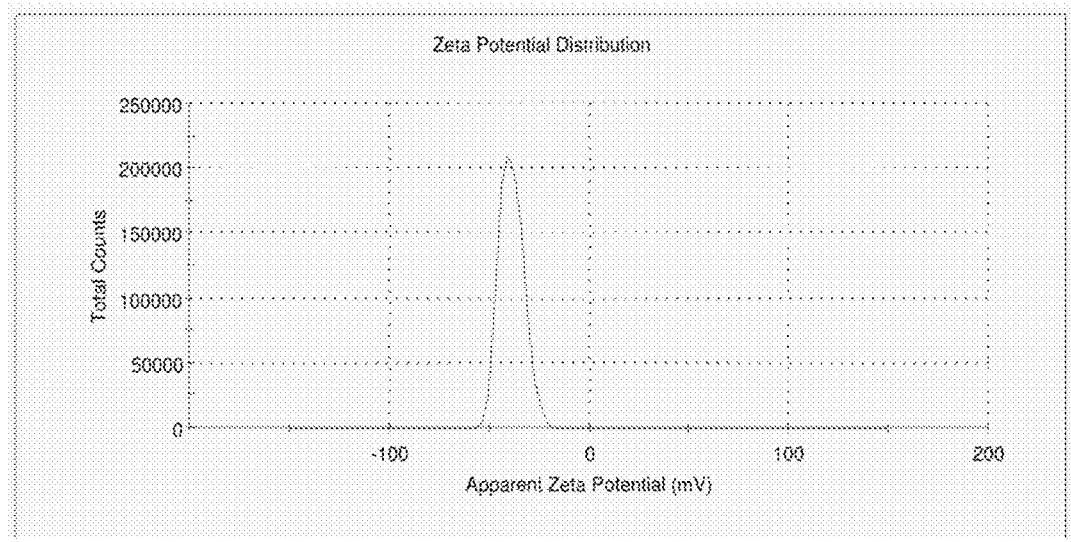
FIGS. 1A and B show the zeta potential of metal complex activated nanoparticles (1A) in comparison to heparin coated metal complex particles (1B)

In this patent specification, the terms 'comprises', 'comprising', 'includes', 'including', or similar terms are intended to mean a non-exclusive inclusion, such that a method or composition that comprises a list of elements does not include those elements solely, but may well include other elements not listed.

As used herein, the term "coordination complex" refers to the product of a Lewis acid-base reaction in which neutral molecules or anions (ligands) bond to a central metal atom (or ion) by coordinate covalent bonds. The ligands operate as Lewis bases—they contain at least one pair of electrons to donate to a metal atom/ion. The central metal atoms/ions are Lewis acids—they can accept pairs of electrons from Lewis bases.

As used herein, the term "coordinate bond" refers to coordinate covalent bonding which is a covalent bond in which one atom (i.e., the donor atom) supplies both electrons. It is considered to be equivalent to the terms "dative covalent bond" and "dipolar bond" and may be used interchangeably herein with these terms.

The term "metal coordination complex", as used herein, refers to metal coordination complexes, or "metal complexes" or "coordination complexes", comprising a metal having coordinate covalent bonds to electron donor ligands. While not wishing to be bound by any particular theory, the metal coordination complex is believed to bond with the substrate via coordination or some alternative binding via ligands which are already coordinated to the metal complex. Subsequently, the residual coordination potential remaining on the metal complex substrate binds the functional heparin, and any further co-bonding agents which may be present, via displacement of one or more of its existing coordination ligands. The term may be used in reference to the metal coordination complex before bonding occurs to either the substrate or the functional heparin, unless the context clearly indicates otherwise, but it will be appreciated that the species formed after such bonding events will also be metal coordination complexes i.e. only the nature of the ligands has changed.

As used herein, the term "substrate" or "substrate with a hemocompatible coating" refers to a substrate, such as a medical device, microparticle, nanoparticle, assay products such as plates and other devices, blood handling product, and like materials, which has at least one surface which requires functionalisation to demonstrate hemocompatibility. It will therefore be understood that the substrate is one which has a surface which, after exposure to the metal coordination complex and functional heparin via the presently disclosed method, will become hemocompatible.

Unless defined otherwise, all technical and scientific terms used herein have the same meaning as would be commonly understood by those of ordinary skill in the art to which this invention belongs.

According to a first aspect of the invention, there is provided a substrate having a hemocompatible coating comprising:

(a) a metal coordination complex bonded to a surface of the substrate; and (b) a functional heparin layer bonded directly to the metal coordination complex.

In one highly preferred embodiment, the metal coordination complex is an oligomeric metal coordination complex.

The metal coordination complex may be a simple coordination complex such as could be formed using monomeric chromium chloride solution. Such solutions are capable of bonding to a variety of substrate surfaces and also to a functional heparin. However, for reasons described herein it is preferred that an oligomeric metal coordination complex is used and so while the embodiments discussed refer to such a complex but it will be understood that the invention is not so limited. Particularly, preferably more than 75%, preferably more than 80%, preferably more than 85%, preferably more than 90%, preferably more than 95%, preferably more than 98 or 99% of metal ions in the metal coordination complex on the substrate are in the form of oligomeric metal coordination complexes.

It will be understood that the functional heparin layer is bonded to the metal coordination complex on a face thereof substantially opposite the face of the metal coordination complex which is bonded to the substrate surface. That is, the metal coordination complex effectively forms a layer over the substrate surface and the functional heparin layer is coated on top of this metal coordination complex layer.

The substrate may, in one embodiment, be selected from a medical device, a nanoparticle and a blood handling product.

The medical device is preferably an implantable medical device which may be any suitable device that can be implanted in a human or veterinary patient. Examples of such implantable devices, without limitation thereto, include self-expandable stents, balloon-expandable stents, stent-grafts, grafts (e.g., aortic grafts), artificial heart valves, cerebrospinal fluid shunts, pacemaker electrodes, and endocardial leads. The underlying structure of the device can be of virtually any design and formed from any material. The device can be made of a metallic material or an alloy thereof. Devices made from bioabsorbable or biostable polymers could also be used with the embodiments of the present invention.

Nanoparticles requiring hemocompatibility may be those for use in biomedical applications such as in therapeutics, drug delivery, biosensors, imaging, and the like. It is important that any such nanoparticle-related products minimise the immune response or activation of the complement cascade, which as a consequence, may lead to poor performance in its intended use such as elimination of the nanoparticles from the blood. The nanoparticle may be formed from a wide range of materials including metals, metal alloys, ceramics, silica polymers, and the like.

The blood handling product may be selected from blood collection and storage tubes including vacutainers, flexible bags and other containers for storage and delivery of blood to patients via a transfusion, blood oxygenators, blood delivery lines, syringes and the like.

Assay products may include lateral flow devices, microfluidic devices and other device components used in immunoassay and molecular diagnostics. In particular, clotting of small blood samples in Point of Care (PoC) devices may reduce sample volumes leading to poor performance in its intended use, such as decreased sensitivity, and so use of the present invention may reduce or alleviate such issues.

In one embodiment, the surface of the substrate to be made hemocompatible is simply a surface of the 'as formed' substrate and so will be formed of the material the substrate is substantially comprised of. In alternative embodiments, and possibly due to biocompatibility requirements, the natural surface of the 'as manufactured' substrate, such as a medical device or blood handling product or nanoparticle, may first be coated with a metal or polymeric coating to form the substrate surface to which the oligomeric metal coordination complex is bonded.

In one embodiment, the substrate surface is selected from a metal, a metalloid, a metal alloy, a metalloid alloy and a polymeric surface.

In one embodiment, the substrate surface may comprise a metal or metalloid, each of which may be part of an alloy, selected from cobalt, chromium, iron, tantalum, nickel, titanium, silicon, carbon, aluminium, platinum, iridium, gold, magnesium and molybdenum.

In one embodiment, the metal alloys may be selected from cobalt and/or chromium alloys, stainless steel, high nitrogen stainless steel, tantalum alloys, nickel-titanium alloys, platinum-iridium alloys, gold alloys and magnesium alloys.

In one embodiment, the substrate comprises a polymeric material which is a hydrophobic polymer. Representative hydrophobic polymers may be selected from the group consisting of PVC, poly(ester amide), polystyrene-polyisobutylene-polystyrene block copolymer (SIS), polystyrene, polyxylene, polyisobutylene, polycaprolactone (PCL), poly(L-lactide), poly(D,L-lactide), poly(lactides), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly(trimethylene carbonate), poly (ortho ester), polyphosphazenes, poly (phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly (vinylidene fluoride-co-chlorotrifluoroethylene) (PVDF-CTFE), poly(butyl methacrylate), poly(methyl methacrylate), poly(methacrylates), poly(vinyl acetate), poly (ethylene-co-vinyl acetate), poly(ethylene-co-vinyl alcohol), poly(ester urethanes), poly(ether-urethanes), poly (carbonate-urethanes), poly(silicone-urethanes), poly(2-hydroxyethyl methacrylate), PVDF-Solef® (polyvinylidenefluoride), cyclic olefin copolymers/polymers (COC or COP), poly(urea-urethanes) and cross-linked polymers comprising any two or more of these polymers.

In one alternative embodiment, the polymeric material is a hydrophilic polymer. Representative hydrophilic polymers may be selected from the group consisting of polymers and co-polymers of hydroxylethyl methacrylate (HEMA), PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, alkoxymethacrylate, alkoxyacrylate, and 3-trimethylsilylpropyl methacrylate (TMSPMA), poly (ethylene glycol) (PEG), poly(propylene glycol), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), hydroxy functional poly(vinyl pyrrolidone), polyalkylene oxide, dextran, dextrin, sodium hyaluronate, hyaluronic acid, heparin, elastin, chitosan and cross-linked polymers comprising any two or more of these polymers.

The substrate may be in the form of nano- and micro-sized particles, fibres, tubes, sheets, mesh, membranes, and any other fabricated or moulded shape.

It is a further advantage of the present invention that the oligomeric metal coordination complex can be bonded to a wide variety of metal, metalloid and polymeric substrate surfaces of all shapes and sizes.

In particular, by changing the nature of the metal salts and reaction environment, it is possible to modulate the binding of the metal coordination complexes, oligomeric or otherwise, to any available electron donating groups on the substrate surface, and present a coordination layer to bind functional heparin and closely related polysaccharides, with or without other synthetic and/or biological reagents and polymers being present.

The metal coordination complexes can coordinate to any electron-donating groups on the surface of the substrate. Even substrate materials purported not to have election donating groups often have such groups as a consequence of our oxygenated atmosphere. Accordingly, the substrate material includes a surface having electron-donating groups, and the metal ions of the metal coordination complexes are bound via a dative bond to these electron-donating groups of the substrate surface material. Suitable electron-donating surface moieties include oxides. In certain embodiments, the substrate comprises electron donating groups selected from carboxylic acid functionalised, amide functionalised, amine functionalised, hydroxyl functionalised, and aldehyde functionalised.

Where the substrate surface is predominantly hydrophobic with little or no electron donating groups to adequately bind the metal coordination complexes, the metal coordination complexes can be modified to improve binding by having one or more co-ordination sites occupied by a hydrophobic ligand for binding the metal complex to the hydrophobic surface, wherein the hydrophobic ligand binds to the hydrophobic surface by non-covalent and non-coordinative interactions, and the residual metal co-ordination sites are available to present a coordination layer to bind functional heparin and other related polysaccharides, with or without other synthetic or biological polymeric agents.

Therefore, in one embodiment, where there are little or no electron-donating groups on the surface of the substrate, at least one ligand of the metal coordination complex can be can be a hydrophobic ligand (R-X), where X coordinates to the metal ion and so where X may be any electron-donating group that is able to form a co-ordination bond with the metal ion. The group "R" may be independently selected from alkyl, heteroalkyl, alkenyl, alkynyl, cycloalkyl, heterocycloalkyl, alkylcycloalkyl, heteroalkylcycloalkyl, aryl, heteroaryl, aralkyl and heteroaralkyl, which groups are optionally substituted. In accordance with this embodiment, "R" is preferred to have more hydrophobic character. Further, the R group may also incorporate moieties selected from a conjugated diene containing group, a polyaromatic or heteroaromatic containing group, a nitrogen containing group, an oxygen containing group, or a sulfur containing group. Preferably the "R" group is a short polymer such as shorter versions of polymeric binders such as polyvinylidene fluoride (PVDF), poly(styrene butadiene), polyethylene and its copolymers, polypropylene and its co-polymers, and polyvinyl chloride. Such substituted metal complexes and their uses are described in further detail in WO 2015/192183 A1

Further, it is common that many substrates have differing distribution and density of electron donating groups that can act as coordinating ligands. If so, two step procedures may be used to produce a uniform layer of metal complexes on a substrate despite any underlying differences in the degree or distribution of electron donating groups on the substrate. In this case, the first step involves addition of metal complexes that coordinate to any available sites on the substrate. The second step involves addition of metal complexes having hydrophobic substituents so that hydrophobic interactions occur where there are no coordination sites on the substrate. Using both steps, a substantially complete metal complex surface with coordination potential to bind heparin and other co-bonding agents is produced.

The number or density of coordination sites on a substrate can be further amplified by addition of a polymer containing ligands such as polyacrylic acid, methacrylic acid, and the like. This results in a substrate having more electron donating groups per unit surface area on which a higher density of metal-ion complexes can form, thereby increasing the number of coordination sites per heparin molecule. By selection of the polymer ligand type (functionalised with, for example, carboxylic acid, hydroxyl, sulphonic acid, and like electron-donating groups) and structure (linear, branched, comb, etc.) and the number of polymer layers formed, completely different surfaces can be formed on a substrate for heparin binding thereby providing for a high level of tailoring to individual applications and general versatility.

As generally used herein, the term "functional heparin", refers to components selected from heparin, a fraction thereof, a heparin analogue, a heparin derivative, low molecular weight heparin (LMWH) or other molecules which demonstrate the same or similar anticoagulant functional outcomes to heparin itself. The term "heparin" as used herein similarly refers to a heparin molecule, a fragment of the heparin molecule, or a derivative of heparin etc. Heparin derivatives can be any functional or structural variation of heparin. Representative variations include alkali metal or alkaline—earth metal salts of heparin, such as sodium heparin (e.g., hepsal, dalteparin or pularin), potassium heparin (e.g., clarin), lithium heparin, calcium heparin (e.g., calciparine), magnesium heparin (e.g., cutheparine), and low molecular weight heparin (e.g., ardeparin sodium). Other examples include heparin sulfate, heparinoids, heparin based compounds and heparins having a hydrophobic counter-ion.

By "low molecular weight heparin or LMWH" is meant a functional heparin class which consist of only relatively short polysaccharide chains, relative to natural heparin. LMWHs may be defined as heparin salts having an average molecular weight of less than 8000 Da and for which at least 60% of all chains have a molecular weight less than 8000 Da. They are typically obtained from unfractionated heparin (UHF) by chemical or enzymatic depolymerization to yield fragments that are approximately one third the size of heparin (Hirsch; Circulation; 1998; 98: 1575-1582). Like UFH, they are heterogeneous with respect to molecular size and anticoagulant activity. LMWHs have a mean molecular weight of 4000 to 5000, with a molecular weight distribution of 1000 to 10,000. Table 1 below is a comparison of various LMWH suitable for use as the functional heparin, and their method of preparation but the person of skill in the art will appreciate that this list is not exhaustive and other such LMWH products are freely available.

TABLE 1

LMWH products and their respective preparation methods.

| Preparation | Method of Preparation | Mean Molecular Weight |
| --- | --- | --- |
| Ardeparin (Normiflo) | Peroxidative depolymerization | 6000 |
| Dalteparin (Fragmin) | Nitrous acid depolymerization | 6000 |
| Enoxaparin (Lovenox) | Benzylation and alkaline depolymerization | 4200 |
| Nadroparin (Fraxiparine) | Nitrous acid depolymerization | 4500 |
| Reviparin (Clivarine) | Nitrous acid depolymerization, chromatographic purification | 4000 |
| Tinzaparin (Innohep) | Heparinase digestion | 4500 |

In one embodiment, the metal coordination complex comprises a metal ion selected from the group consisting of chromium, ruthenium, iron, cobalt, platinum, scandium, titanium, vanadium, manganese, nickel, copper, molybdenum, zinc, aluminium, zirconium and rhodium.

In certain embodiments, the metal coordination complex comprises a metal ion selected from the group consisting of chromium, ruthenium, iron, cobalt, aluminium, zirconium and rhodium.

In one embodiment, the metal ion is a chromium ion.

The metal ion may be present in any applicable oxidation state. For example, chromium is known to have the following oxidation states of I, II, III, IV, V, or VI. In an embodiment in which the metal ion is a chromium ion, it is preferred that the chromium has an oxidation state of III.

In certain embodiments, mixtures of different metal ions may be used, for example, to form a plurality of different metal-ligand complexes which may or may not be associated or which may together make up the oligomeric metal coordination complex. In such cases, it is preferred that at least one metal ion is chromium.

Metals are known to form a range of metal-ligand complexes. In one embodiment, the metal coordination complex comprises a ligand forming the complex with the metal. Ligands for forming the metal coordination complex are those that include nitrogen, oxygen, or sulphur as dative bond forming groups. More preferably, the dative bond forming groups are oxygen or nitrogen. Even more preferably, the dative bond forming group is an oxygen containing group. Still even more preferably, the oxygen containing group is selected from the group consisting of oxides, hydroxides, water, sulphates, phosphates, carboxylates, sulphonic acids and phosphonic acids.

In an embodiment, the ligand is a mono-, di-, or tri-atomic ligand. Preferably, the ligand is an oxygen containing species such as an oxide, a hydroxide, or water; wherein the dative bond forming group is oxygen.

In one embodiment the ligand is an inorganic ligand. Preferably the ligand is an oxo ligand.

When, in preferred embodiments, the metal coordination complex is oligomeric then the layer of oligomeric metal coordination complex is stabilised, in part, by cross-linking of the metal ions with each other to form the larger oligomeric metal-ligand complexes. This results in the oligomeric metal coordination complex being stable not only to conditions prevalent in the body but also to physical processes, such as sterilisation, to which the medical device will be subjected.

In one embodiment, the ligand is a bridging compound that is datively bonded to at least two of the metal ions. Preferably, this results in the formation of the oligomeric metal-ligand complex.

In one exemplary embodiment, the metal coordination complex is an oxo-bridged chromium (III) complex. This complex may optionally be further oligomerised with one or more bridging couplings such as carboxylic acids, sulphates, phosphates and other multi-dentate ligands.

In any of the embodiments described herein, the functional heparin layer is bonded directly to the oligomeric metal coordination complex through one or more coordinate bonds.

In one embodiment, the metal coordination complex is not covalently bonded to a functional group of the substrate.

In certain embodiments, the metal coordination complex does not comprise silver as a metal.

In embodiments, the metal of the metal coordination complex is not released from the complex to any substantial degree. That is, at least 70%, 80%, 90%, 95%, 96%, 97%, 98% or 99% of the metal remains within the metal coordination complex.

In preferred embodiments, the substrate surface does not require a pre-treatment step to establish a more reactive surface for bonding with the metal coordination complex.

Suitably, the metal coordination complex is bonded directly to and achieves adherence to the substrate surface.

In one embodiment, a separate layer or treatment is not required to be applied to the metal coordination complex to achieve adherence to the substrate surface.

In certain embodiments, the metal coordination complex to which the functional heparin is bound is not, itself, a particle, nanoparticle or other substrate as defined herein. That is, the metal coordination complex is a separate component and is of a different character to the substrate surface to which it binds.

It will be understood that the metal coordination complex will be a separate layer, to the substrate surface, which is coordinately or datively bonded to that substrate surface. Therefore even if, for example, both the substrate surface and the metal coordination complex comprise chromium, it will be understood that the metal coordination complex forms a layer which is separate but bonded to the substrate surface.

It is a significant advantage of the present invention, and in particular the use of the oligomeric metal coordination complex, that the oligomeric metal coordination complex enables avidity bonding of the functional heparin and other related polysaccharides. That is, heparin is directly bonded to the oligomeric metal coordination complex through multiple interactions the accumulated strength of which results in anchoring of heparin and related polysaccharides to the oligomeric metal coordination complex as if it were bonded via standard covalent bonding. However, any individual coordination bond between the metal ion in the metal coordination complex and heparin or other related polysaccharides is relatively weak and can break as a result of some local stressor such as binding of antithrombin. It is believed that functionality of heparin is maintained as a consequence of these multiple coordination bonds breaking and reforming according to the prevailing conditions. But, it is highly unlikely that the totality of coordination bonds will all break at the same time thereby ensuring that the functional heparin remains coordinated to the substrate surface. In brief, this approach maintains heparin functionality with the simplicity of non-covalent methods, such as physical adsorption or ionic interactions, and the stability of covalent methods on almost any substrate without complex chemical modifications to either the substrate surface or to the functional heparin.

It could not have been predicted with any reasonable degree of certainty, based on the present understanding in the art, that functional heparin could have been bonded to the metal coordination complex and yet still display a useful level of functionality rather than simply becoming strongly bound but non-functional due to that binding.

Particularly, it is surprising that this stable bonding could be achieved considering the relatively small molar mass of heparin, and especially its lower molecular weight versions, while still maintaining heparin functionality. Overall strength of binding is dependent on avidity and without the need for further functionalisation of the heparin molecule to display additional coordination groups to enable bonding to the metal coordination complex, a functional hemocompatible coating is formed, in preferred embodiments, by a simple bonding to the metal coordination complex which is itself bonded, directly or otherwise, to the substrate surface.

Avidity binding is highly stable with increasing number of coordination points between the metal coordination complex activated substrate surface and the electron donating groups in heparin. A further advantage of the present invention is that the strength of the bond can be tuned by manipulating the binding conditions, the relative concentrations of the species and the character of the oligomeric metal coordination complex such that if, for example, UHF is employed as the functional heparin then rather than the entire molecule being bonded to the oligomeric metal coordination complex it may be bonded only at certain points and the remainder of the UHF left available, in a conformational sense, for the expression of anticoagulant character.

Further, the number or density of coordination points per unit surface area can be manipulated by the concentration and the type of oligomeric metal coordination complexes with respect to the substrate surface that may have different densities of electron donating groups. Subsequently, the concentration of functional heparin (or to be specific, the number of electron donating species in the molecule) will determine the level of coordination between the substrate surface and the functional heparin molecule.

The strength of individual coordination bonds between the metal complex and a functional heparin ligand can be further manipulated by variations in temperature and time during exposure of heparin to the metal complex. Incubation at higher temperatures such as, for example, 30° C. to 140° C., 40° C. to 120° C. or 50° C. to 100° C., including about 40° C., 50° C., 60° C., 70° C., 80° C., 90° C. and 100° C., can further strengthen the coordinate bonds to heparin, thereby increasing its stability on any given substrate. In certain embodiments, this can allow for release of a co-bonding agent from the substrate while substantially maintaining the functional heparin bound to the substrate.

In one embodiment, the above variables can be manipulated to allow release of heparin off the substrate overtime as a consequence of limited coordination between the heparin and substrate. In another embodiment, the substrate hemocompatible coating may further comprise a co-bonding agent. It is intended that the co-bonding agent will not demonstrate any clinically significant level of anti-thrombogenic activity and so it is an agent separate and distinct from the various functional heparins considered herein. The co-bonding agent may, in one embodiment, simply act as a 'spacer' to prevent crowding or binding of key functional sites on the heparin to the metal coordination complex to thereby ensure functionality is maintained following bonding. In other embodiments, the co-bonding agent may be a biologically active agent. In certain embodiments, the co-bonding agent may be selected from a synthetic or biological polymer, a labelling agent and a small molecule drug.

In one embodiment, the co-bonding agent may be a polymer selected from the group consisting of polysaccharides or other polymers, both biological and synthetic, containing electron donating groups. Apart from helping to control the degree of coordination between the metal coordination complex covered substrate surface and functional heparin, such polymeric co-bonding agents can impart further non-thrombogenic functional properties to the substrate in addition to the anti-thrombogenic properties of heparin.

The co-bonding agent may also include other biological polymers such as antibodies and other proteins and peptides that may act as a probe, a targeting agent or a depletion agent to give multi-functionality to the coated substrate surface. In specific embodiments, the co-bonding agent is selected from a protein, a carbohydrate, a lipid, a polynucleotide, a drug, a labelling agent, a synthetic polymer, a nanoparticle and a cell. Together, the flexibility of this coordination approach allows more complicated structures such as an Extracellular Matrix (ECM) or other biomimetic surfaces to be created on any substrate.

The ratio of functional heparin to the co-bonding agent will depend on the relative molecular weight of the species as well the binding affinity of the various electron donating ligands that constitute part of the functional heparin and co-bonding agent.

In another embodiment, different heparins (e.g., those having high or low affinities), having stronger or weaker binding to substrate, having different co-bonding agents, or being localised on different sections of the substrate can be employed to bring greater flexibility in tailoring the hemocompatible coatings to specific applications.

A second aspect of the invention provides for a method of forming a hemocompatible coating on a substrate including the steps of:

(a) forming a metal coordination complex on a surface of the substrate;

(b) coating the metal coordination complex with a functional heparin such that the functional heparin bonds directly to the metal coordination complex, to thereby form the hemocompatible coating on the substrate.

In one embodiment, the method may further include the step of contacting the metal coordination complex with a co-bonding agent.

The metal coordination complex, the substrate, substrate surface, co-bonding agent and the functional heparin may all be as described in relation to the first aspect.

The functional heparin bonds directly to the metal coordination complex through one or more coordinate bonds.

Preferably, the metal coordination complex is an oligomeric metal coordination complex.

The metal coordination complex may form a layer on the surface of the substrate or, in further embodiments, form multiple layers as part of a more complex surface coating.

In preparing to form the metal coordination complex the metal ion which will be a component of the metal coordination complex may be associated with a counter-ion (such as an anion selected from the group consisting of chloride, acetate, bromide, nitrate, perchlorate, alum, fluoride, formate and sulphate), which can be co-ordinating or non-coordinating. In one embodiment the counter-ion is a non-coordinating anion. In another embodiment the counter-ion is a coordinating anion.

The metal-ligand complexes which form the oligomeric metal coordination complex can generally be formed by providing conditions for forming electron donating groups for bridging or otherwise linking or bonding two or more metal ions. This can be done by providing a pH below pH 7, preferably about 1.5 to 6, preferably about 2 to 5 to the composition formed from the contact of the metal-ligand complexes with the surface of the active material. Alternatively, if an oligomeric metal coordination complex is not desired then the pH can be controlled to discourage oligomer formation.

Various chromium salts such as chromium chloride, chromium nitrate, chromium sulphate, chromium perchlorates, may be used to form the metal-ligand complex. These salts are mixed with an alkaline solution, such as potassium hydroxide, sodium bicarbonate, sodium sulphite and ammonia to form different metal-ligand complexes. Organic reagents that can act as bases such as ethylene diamine, bis(3-aminopropyl)diethylamine, pyridine, imidazoles, can also be used as a source of the coordinating ligands. The size and structure of the metal-ligand complex can vary with pH, temperature, solvents and other conditions.

The metal-ligand complex is further stabilised by cross-linking the metal ions with each other to form larger oligomeric metal coordination complex. Such oligomeric metal coordination complexes can be pre-formed and applied to the substrate of the medical device, or formed in-situ on the substrate. In this case, the ligands are able to form multiple dative bonds with multiple metal ions, to effectively bridge or cross-link the metal ions. That is, the ligand may form dative bonds with two or more metal ions, thereby linking one metal ion to another metal ion.

Exemplary oxo-bridged chromium structures are provided below:

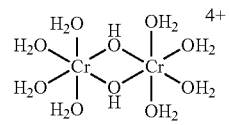
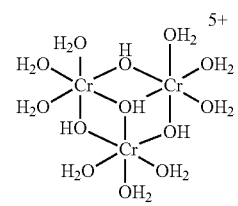
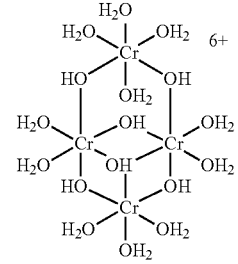

On application to the substrate, at least one of the water or hydroxyl groups on each of the metal-ligand complexes is replaced by a dative bond with the surface of the active material. This is illustrated below wherein "X" represents the dative bond to the substrate.

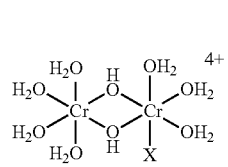
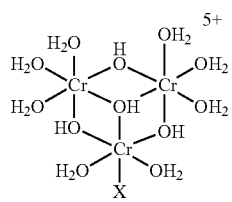
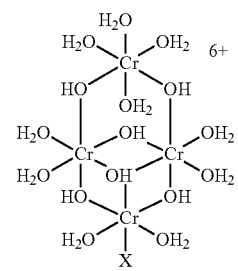

It will also be appreciated that multiple water or hydroxyl groups may be replaced by a dative bond with the substrate surface, for example each chromium ion may form a dative bond with the substrate surface of the medical device or other hemocompatible substrate.

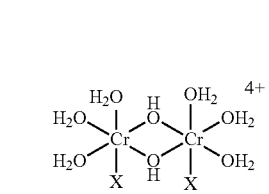
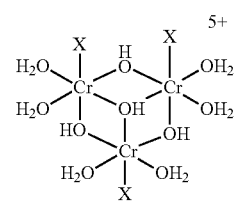

-continued

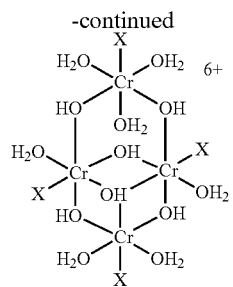

In addition, the water and/or hydroxyl groups may be replaced by a dative bond with another component of the coating, such as with the co-bonding agent.

In the case where a substituted oligomeric metal coordination complex is preferred such as for hydrophobic substrate surfaces, the water and/or hydroxyl groups may be replaced by a dative bond with a hydrophobic ligand for binding the metal coordination complex to the hydrophobic surface, wherein the hydrophobic ligand binds to the hydrophobic surface by non-covalent and non-coordinative interactions, and the residual co-ordination sites are available to present a coordination layer to bind the functional heparin and other related polysaccharides, with or without other co-bonding agents, such as synthetic or biological polymeric agents.

It is an advantage of the present invention that the formation of the oligomeric metal coordination complex on the substrate and the bonding of the functional heparin thereto can be carried out on a wide range of surfaces quickly and with relatively straightforward chemistry. Compared with prior art approaches there are minimal concerns regarding compatibility of oligomeric metal coordination complex with substrate and functional heparin component with the oligomeric metal coordination complex. The coating can be formed under relatively mild conditions and is robust enough to survive subsequent sterilisation procedures. The bonding between the oligomeric metal coordination complex and the functional heparin is such that it can be manipulated according to the molecular weight of the functional heparin, the type of and extent of conditions such as temperature under which the oligomeric metal coordination complexes are used, the nature of the substrate surface, and so can, in certain embodiments, be considered permanent.

In one embodiment of the second aspect, the method includes the step of simultaneously coating the metal coordination complex with the functional heparin and the co-bonding agent. More than one co-bonding agent of a different character may be employed.

In an alternative embodiment, the metal coordination complex may initially be coated with the functional heparin and then subsequently coated with the co-bonding agent.

A third aspect of the invention provides for a method of reducing the incidence of thrombosis in a target area of a patient including implanting the substrate with the hemocompatible coating of the first aspect within the target area.

The substrate is preferably a medical device which may be selected from the group consisting of self-expandable stents, balloon-expandable stents, stent-grafts, grafts (e.g., aortic grafts), artificial heart valves, cerebrospinal fluid shunts, pacemaker electrodes, acetabular cups, femoral devices for hip replacements, pins, rods, screws, plates, surgical mesh, contraceptive implants, prostheses and endocardial leads. Such devices and a range of others would be well known to those in the art. It is an advantage of the invention that the oligomeric metal coordination complex can bond to a very wide range of surfaces and so the medical device is not particularly limited by the material it is constructed from.

The manner and procedures for implanting the medical device are well known in the art.

A fourth aspect of the invention resides in a kit comprising:

(c) a vial comprising a solution of a metal coordination complex; and (d) a vial comprising a functional heparin solution;

wherein the solution of the metal coordination complex is adapted to be applied to a surface of a substrate to form a layer thereon and the functional heparin solution is adapted to be applied to the metal coordination complex layer to bind thereto and form a hemocompatible coating on the substrate.

The metal coordination complex, substrate and functional heparin are as defined herein in relation to the first and/or second aspects.

The kit is for use in accordance with the method of the second aspect.

The various features and embodiments of the present invention, referred to in individual sections above apply, as appropriate, to other sections, mutatis mutandis. Consequently features specified in one section may be combined with features specified in other sections as appropriate.

The following examples are provided by way of illustration and are in no way limiting upon the scope of the invention.

EXPERIMENTAL

Examples 1-3: Metal Complex Activated Particles

Example 1: Zeta Potential Measurements on Heparin Bound to Oligomeric Metal Complex Coated Nanoparticles A. Preparation of Metal Coordination Complexes on Nanoparticles Magnetic nanoparticles of 200 nm dimensions purchased from Allrun Nano Science & Technology, Cat No PM3-020 were coated with oligomeric metal complexes as follows. In brief, chromium perchlorate hexahydrate (45.9 g) was dissolved into 480 mL of purified water and mixed thoroughly until all solid dissolved. Similarly, 8 mls of ethylene diamine solution was added to 490 mL of purified water. The solutions were combined and stirred overnight at room temperature, and then left to equilibrate to a pH of approximately 4.5.

The nanoparticles were allowed to reach room temperature and vortexed for 30 seconds. 1000 μL of particle concentrate was dispensed into a microtube. The tube was placed on a magnetic rack for 1 minute and the supernatant was carefully removed and discarded from the particle pellet. The particle pellet was resuspended with 100 μl of deionised water with 0.1% pluronic based surfactant, then adding this to 900 μl of the metal complex solution to reach a final concentration of 90 mM metal complex+0.1% pluronic based surfactant. This was left overnight at room temperature with rotation. Separate particles on a magnet for 1-2 minutes and carefully remove the supernatant. Resuspend 1000 μl of diluted metal complexes solution to the tube. Vortex for 30 seconds, and sonicate for 5 minutes on high. Store the metal complex activated particles at 2-8° C.

B. Conjugation of Heparin to Metal Complex-Activated Nanoparticles.

Allow all reagents to come to room temperature. Stock heparin sodium porcine mucosa solution, 50 mg/mL was diluted to 800 µg/mL in 25 mM MES buffer, pH5.2. Vortex stock metal complex activated particles for 10 seconds at high speed and bath sonicate for 5 minutes. Aliquot 100 µL of the stock metal complex activated particles (10 mg/mL) to a microtube. Place the tube on the magnetic rack for 1-2 minutes and remove supernatant. Remove the particles tube from magnetic rack and add 100 µL of 25 mM MES buffer, pH5.2. Wash the magnetic particles 2×100 µL of 25 mM MES buffer, pH5.2. Replace 100 µL of 25 mM MES buffer, pH5.2 in the particles tube. Vortex the metal complex activated magnetic particles for 10 seconds at high speed and pulse spin to ensure the liquid is all at the bottom of the tube. Aliquot 100 µL of 800 µg/mL heparin solution in a new tube and then add the 100 µL of metal complex activated particles into the 100 µL of 800 µg/mL heparin solution. Vortex the particles for 10 seconds at high speed and pulse spin to ensure the liquid is all at the bottom of the tube. Incubate for 60 minutes at room temperature on a rotator. Add 20 µL of 25 mM MES buffer with 10% BSA, pH 5.2 and vortex the particles for 10 seconds at high speed and pulse spin to ensure the liquid is all at the bottom of the tube. Incubate for 60 minutes at room temperature on a rotator. Wash the particles 2×100 µL of 50 mM TBS, 0.05% Pro-Clin300, pH8.0 and stored in the same buffer.

C. Zeta Potential of Heparin Bound to Metal Complex-Activated Nanoparticles.

Allow heparin coated magnetic particles to reach room temperature. Vortex the heparin coated magnetic particles for 10 seconds at high speed and pulse spin to ensure the liquid is all at the bottom of the tube. Bath sonicate for 2×5 minutes. Dilute the heparin coated particles (10 mg/mL) to 0.05 mg/mL in ddH2O. Add 3.75 µL of 10 mg/mL the particles into 746 µL of ddH2O. Vortex the heparin metal complex coated magnetic particles for 10 seconds at high speed. Add 500 µL of the particles solution to a cuvette. Measure Zeta size of the particles by Nano Series—ZS. Add 750 µL of the particles solution to a Zeta potential cuvette. Measure Zeta potential of the particles by Nano Series—ZS.

Figure 1B:
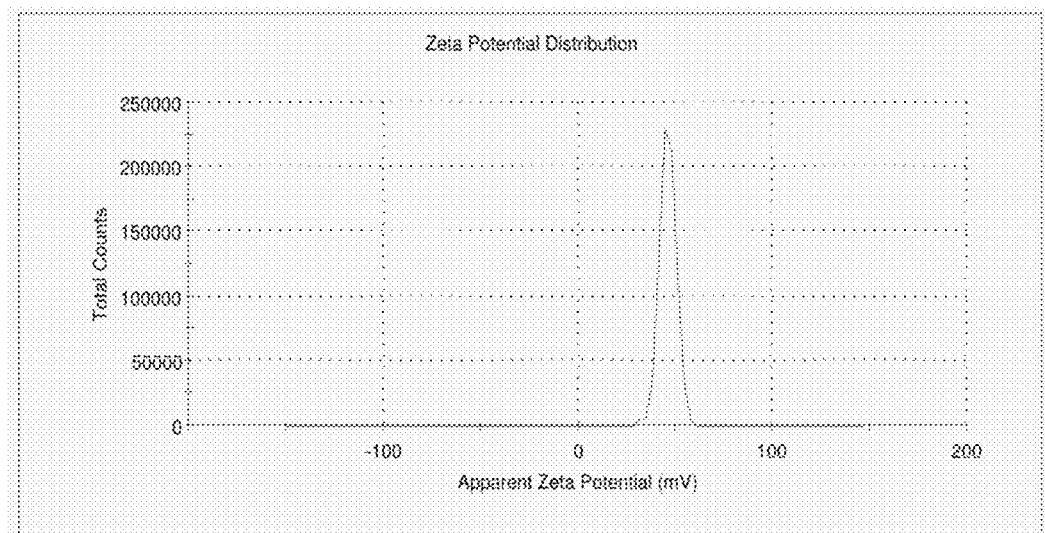

Heparin bound to metal complex activated particles (as formed in step B) and its precursor, metal complex activated particles (as formed in step A) should demonstrate a significantly different charge, changing from a positive (metal coordination complex coated only) to a negative charge (when coated with heparin due to its high level of negative charge). The zeta potential of the two particles are shown in FIG. 1, with FIG. 1A representing the particles coated only with the metal coordination complex and FIG. 1B representing particles coated with heparin bonded onto the metal coordination complex, and the results are summarised in Table 2. Comparison of the zeta potential of the two particles shows, as expected, that the metal complex coated particles are positively charged and the heparin coated particles are negatively charged, thereby confirming both the initial formation of the metal complex on the particles and the subsequent coating, on the selected particle population, of a layer of functional heparin.

TABLE 2

Zeta-average size, Polydispersity Index (PdI) and Zeta potential of heparin coated particles in comparison to the precursor metal complex coated particles without heparin.

| Sample | Z-Average (d · nm) | PdI | Zeta Potential (mV) |
| --- | --- | --- | --- |
| Metal complex coated particles | 246.3 | 0.105 | 45.9 |
| Heparin coated particles | 248.3 | 0.06 | −39.1 |

Example 2: Chemiluminescent Loading Assay of Heparin Coated Nanoparticles

A. Preparation of Heparin Bound Magnetic Particles.

Heparin bound to metal coordination complex activated nanoparticles (200 nm) were formed as described above. To act as a control, Streptavidin MyOne Particles from Life Technologies (Cat No: 65001) (10 mgs/ml) were coupled with biotinylated Heparin as summarised below.

All reagents were allowed to come to room temperature. Stock Heparin-Biotin sodium solution (1 mg/mL) was diluted to 800 µg/mL in 10 mM PBS buffer, pH7.4. Vortex the stock Streptavidin MyOne Particles for 10 seconds at high speed. Aliquot 100 µL of the streptavidin MyOne particles (10 mg/mL) to a microtube. Place the tube on the magnetic rack for 1 minute and remove supernatant. Remove the particles tube from magnetic rack and add 100 µL of Coupling Buffer. Wash the magnetic particles 2×100 µL of 10 mM PBS buffer, pH7.4. Replace 100 µL of 10 mM PBS buffer, pH7.4 in the particles tube. Vortex the streptavidin magnetic particles for 10 seconds at high speed and pulse spin to ensure the liquid is all at the bottom of the tube. Aliquot the 100 µL of 800 µg/mL heparin-biotin solution in a new tube and then add the 100 µL of the streptavidin MyOne particles into the 100 µL of 800 µg/mL heparin-biotin solution. Vortex the particles for 10 seconds at high speed and pulse spin them to ensure the liquid is all at the bottom of the tube. Incubate for 30 minutes at room temperature on a rotator. Wash the particles 2×100 µL of 10 mM PBS, 0.1% BSA, 0.05% ProClin300, pH 7.4 and store in the same buffer.

B. Heparin Loading Assay.

A heparin loading assay on metal coordination complex activated particles was performed according to the procedure below. Allow all reagents to come to room temperature. Dilute the stock anti Heparin (MAB2040 anti Heparin/Heparin Sulphate, Millipore) to 10 µg/mL in TBST, 0.05% Tween 20, 1% BSA, pH8. Heparin coated (200 nm) Magnetic Particles (10 mg/mL) and Biotin-Heparin/Streptavidin MyOne Particles (10 mg/mL) (Streptavidin MyOne from Life Technologies) were vortexed for 10 seconds at high speed and bath sonicated for 1 minute at high speed. Dilute the particles to 0.2 mg/mL in TBST, 0.05% Tween 20, 1% BSA, pH8. Add 50 µL of 10 µg/mL anti Heparin solution into row A to F of column 1 to 4 of the 96 well white PP plate (Greiner). Add 50 µL of TBST, 0.05% Tween 20, 1% BSA, pH8 into row G to H of column 1 to 4 of the plate. Add 50 µL of 0.2 mg/mL Heparin coated (200 nm) Magnetic Particles into row A to H of column 1 and 2 of the plate. Add 50 µL of 0.2 mg/mL Biotin-Heparin/SAv MyOne Dynabeads into row A to H of column 3 and 4 of the plate. Incubate the plate on plate shaker for 90 minutes at room temperature. Wash the particles with 2×100 µL of TBST, 0.05% Tween 20, pH8. Dilute the stock Goat anti Mouse IgG-HRP (Jackson Immuno Research) to 0.02 ug/mL and 0.01 ug/mL into TBST, 0.05% Tween 20, 1% BSA, pH8. Add 50 µL of 0.02 ug/mL GAM-HRP into row A and B of column 1 to 4 of the plate. Add 50 µL of 0.01 ug/mL GAM-HRP into row C and D of column 1 to 4 of the plate. Add 50 µL of TBST, 0.05% Tween 20, 1% BSA, pH8 into row E to H of column 1 to 4 of the plate.

Incubate the plate on plate shaker for 60 minutes at room temperature. Wash the particles with 4×100 µL of TBST, 0.05% Tween 20, pH8. Add 100 µL of Lumingen PS-atto (Lumingen) to each well (A:B solution=1:1). Incubate, covered from light, at room temperature on the plate shaker for 1 minute. Read the plate on Tecan Analyzer.

Figure 2:
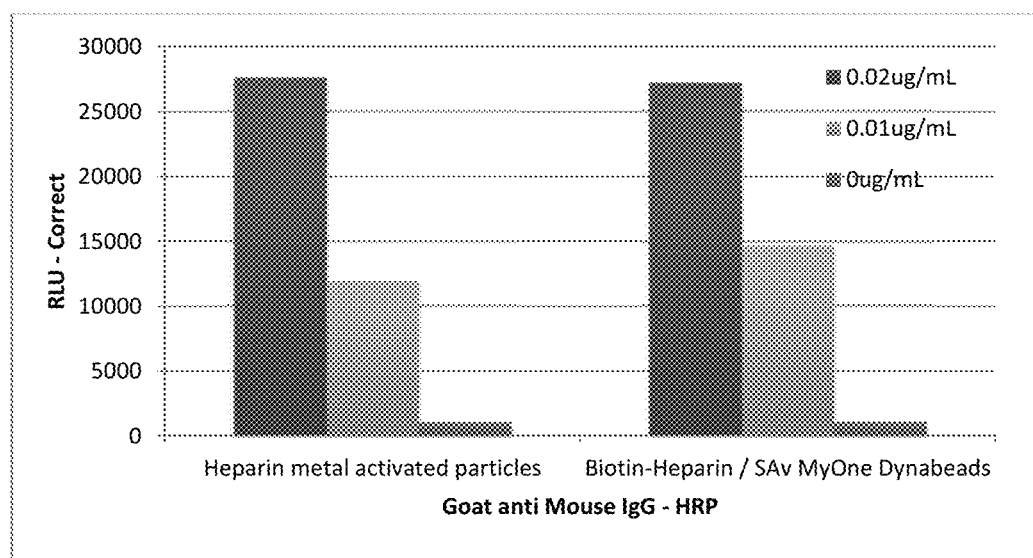
FIG. 2 is a graphical representation of the chemiluminescense loading assay data for two heparin loaded particles, one formed by the method of the present invention.

The chemiluminescense loading data is summarised in Table 3 and FIG. 2. The loading assay data shows comparable loading of heparin using the two Goat anti Mouse IgG-HRP concentrations thereby indicating effective loading of heparin following the method of the present invention.

TABLE 3

Chemiluminescense assay results of the two heparin loaded particles.

| Goat anti Mouse IgG | AVERAGE | | STDEV | | % CV | |
|---|---|---|---|---|---|---|
| | Heparin Metal Complex particles | Biotin-Heparin/SAv MyOne beads | Heparin Metal Complex particles | Biotin-Heparin/SAv MyOne beads | Heparin Metal Complex particles | Biotin-Heparin/SAv MyOne beads |
| 0.02 ug/mL | 36746 | 36116 | 3519 | 1551 | 9.58% | 4.29% |
| 0.01 ug/mL | 21054 | 23651 | 1550 | 1468 | 7.36% | 6.21% |
| 0 ug/mL | 10247 | 10037 | 451 | 1107 | 4.40% | 11.03% |
| Background | 9149 | 8935 | 516 | 442 | 5.64% | 4.95% |

Example 3: Competitive Colorimetric Assay

The approach for qualitative determination of Human Antithrombin (AT) to Heparin is an indirect colorimetric immunoassay. A kit was purchased from Hyphen BioMed (Cat No: 221010) and reagents used are listed below:
Heparin Sodium Porcine Mucosa, 50 mg/mL (Sigma).
Heparin 200 nm Particles prepared as described above by the present method.
Reagent 1 (R1): ATIII (h), Human Antithrombin (AT), 40 ug/mL, 1 mL, BioMed.
Reagent 2 (R2): FXa(b), Purified bovine Factor Xa, 40 ug/mL, 1 mL, BioMed.
Reagent 3 (R3): Chromogenic substrate specific for FXa, 0.8 mg/mL, 5 mL, BioMed.
Reagent 4 (R4): Assay reaction Buffer, Tris 0.05M, NaCl 0.175M, EDTA 0.0075M, at pH8.4, containing PEG t 0.1%, 25 mL, BioMed.
2% citric acid stop solution.

Allow all reagents to come to room temperature. Dilute R1 (1:5) in R4 buffer before use. Dilute R2 (1:5) in R4 buffer before use. Dilute stock heparin to 0.05, 0.025, 0.0125, 0.00625 and 0 (IU/mL) in R4 buffer. Dilute stock heparin coated 200 nm particles to 0.8, 0.4, 0.2, 0.1, 0.05 and 0 (mg/mL) in R4 buffer. Add 25 µL of 0.05 IU/mL heparin solution into row E of column 1 to 3 of the plate. Add 25 µL of 0.025 IU/mL heparin solution into row D of column 1 to 3 of the plate. Add 25 µL of 0.0125 IU/mL heparin solution into row C of column 1 to 3 of the plate. Add 25 µL of 0.00625 IU/mL heparin solution into row B of column 1 to 3 of the plate. Add 25 µL of R4 buffer into row A of column 1 to 3 of the plate. Add 25 µL of 0.8 mg/mL heparin particles into row F of column 4 to 6 of the plate. Add 25 µL of 0.4 mg/mL heparin particles into row E of column 4 to 6 of the plate. Add 25 µL of 0.2 mg/mL heparin particles into row D of column 4 to 6 of the plate. Add 25 µL of 0.1 mg/mL heparin particles into row C of column 4 to 6 of the plate. Add 25 µL of 0.05 mg/mL heparin particles into row B of column 4 to 6 of the plate. Add 25 µL of 0.025 mg/mL heparin particles into row A of column 4 to 6 of the plate. Add 25 µL of R1 solution into all wells of the plate. Incubate the plate on a plate shaker for 2 minutes at 37° C. Add 25 µL of R2 solution into all wells of the plate. Incubate the plate on a plate shaker for 2 minutes at 37° C. Add 25 µL of R3 solution into all wells of the plate. Incubate the plate on a plate shaker for 2 minutes at 37° C. Add 50 µL of 2% citric acid stop solution into all wells of the plate. Place the plate on a plate magnet for 5 minutes, and then transfer the supernatant to the other 96 well lower binding clear plate. Measure the absorbance at 405 nm using Tecan M200PRO.

Figure 3:
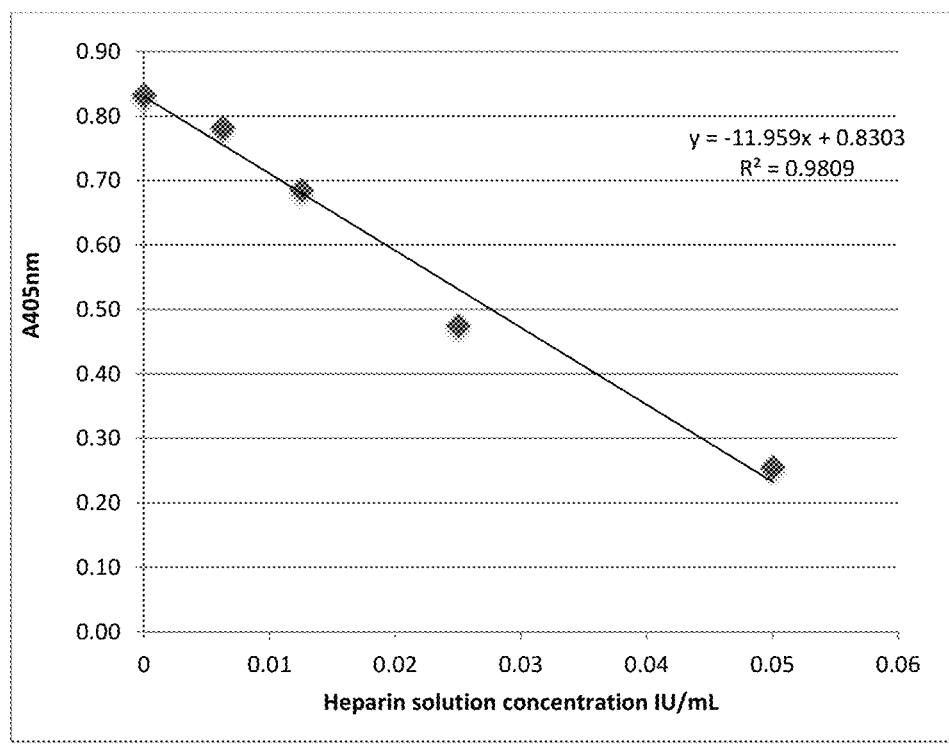
FIG. 3 is a graphical representation of a heparin standard curve on assays with particle substrates.
Figure 4:
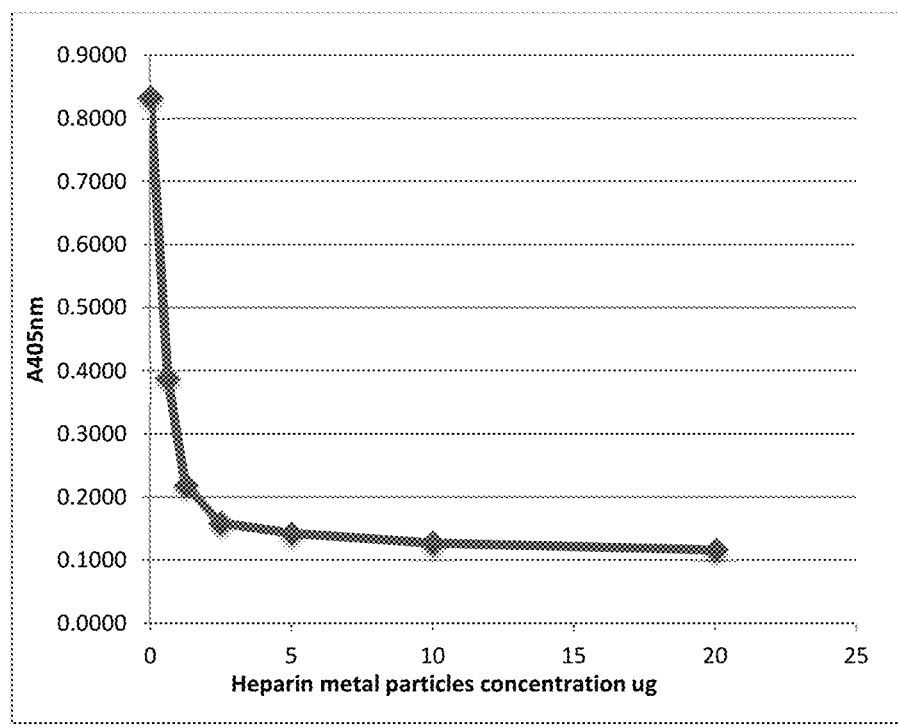
FIG. 4 is a graphical representation of the results of a competitive colorimetric assay for a functional heparin coated onto metal coordination complex activated particles.
Figure 5:
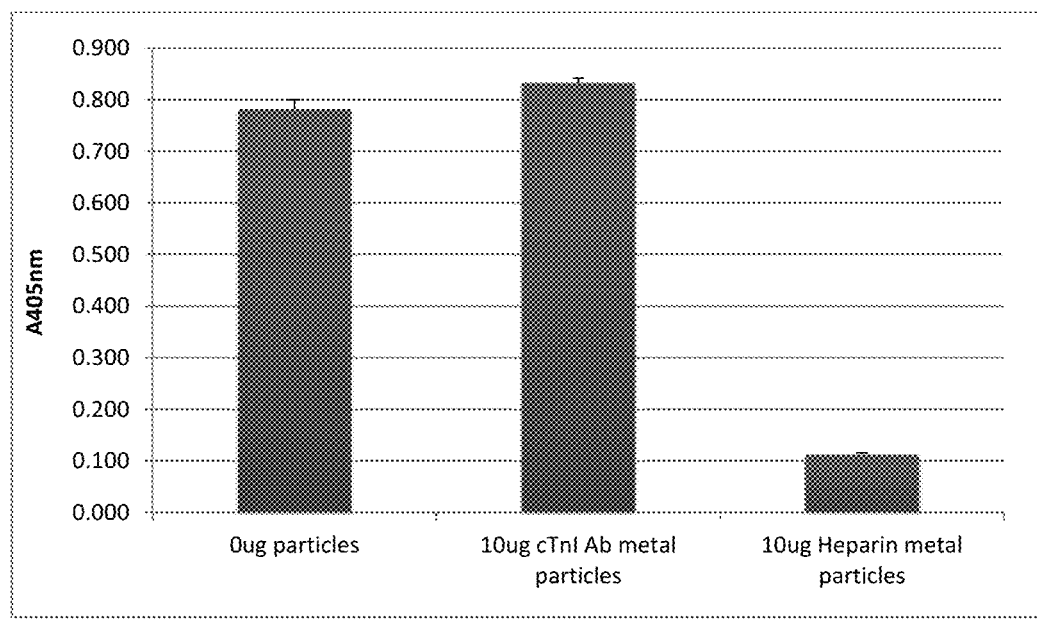
FIG. 5 is a graphical representation of the results of a comparison of 10 ug of anti-troponin MAb coated particles, 10 ug of heparin coated particles, and a control indicating human antithrombin binding.

The heparin standard curve is shown in FIG. 3 and confirmation of functionality of the heparin bound to the metal coordination complex activated nanoparticles is shown in FIG. 4. Increased concentration of the heparin coated particles decreases the specific binding signal, as expected, in this competitive assay. At bug of heparin coated particles, the lowest binding signal is obtained indicating human antithrom bin (0.2 ug) is all bound to these particles. Even 1.25 ug of the particles is sufficient to bind the majority of antithrombin. As a control, 10 ug of anti-troponin (cTnI) MAb coated particles did not show any binding to Human Antithrombin (FIG. 5). The preservation of the functionality of heparin when bound to the metal coordination complex coated substrate of the present invention has thereby been demonstrated.

Examples 4 Onwards—Metal Complex Activated Planar Substrates

Example 4: Heparin and Dalteparin (Low Molecular Weight Heparin) Bound to Oligomeric Metal Complex Coated Polyurethane A. Preparation of Two-Step Metal Complex Coatings on Polyurethane Tubing.

As an example, 3/32×5/32 polyurethane tubing purchased from Ark-plas (USA), Cat No AP01T091PEBLT were coated with oligomeric metal complexes by the two-step approach using two different metal complex formulations. The first metal complex was prepared as previously described in Example 1A. The second substituted metal complex was a lauric acid substituted complex as previously described in WO 2015/192183 A1.

The polyurethane tubing was cut to 0.5 cm sections. Stock oligomeric metal complexes described previously were diluted to 5 mM in ddH$_2$O. Forty segments of 0.5 cm polyurethane tubing were immersed in 10 mL of 5 mM metal complex solution and agitated 30 minutes at 20-25° C. using a rotary mixer. The metal complex solution was aspirated from the container and excess solution drained onto paper towel. Similarly, a 5 mM of lauric acid substituted metal complex in 50:50 isopropanol/water solution (iPOH:ddH$_2$O) was prepared and added to the already metal complex activated polyurethane tubing. Again, the solution was agitated using rotary mixer for 30 minutes at 20-25° C. The solution was aspirated and excess drained onto paper towel. The tubing segments were dried 15 minutes at 20-25° C. and for 15 minutes at 37° C. The tubing was stored in a desiccant cabinet overnight at 20-25° C.

A 0.1% (wt/vol) polyacrylic acid (PAA) solution (450 KDa, Sigma/Product No: 181285-100 g) was made in 10 mMES buffer, pH6. Twenty metal complex coated polyurethane tubing segments were placed into 5 mL of 0.1% polyacrylic acid solution. The tubing was fully immersed in the polymer solution and mixed with a rotary mixer for 30 minutes at 20-25° C. The polymer solution was aspirated and excess drained onto paper towel. The treated tubing segments were then dried for 15 minutes at 20-25° C. and for 15 minutes at 37° C. Treated tubing segments were stored in desiccant cabinet overnight at 20-25° C.

Using the metal complex solutions at 10 mM in ddH$_2$O, twenty segments of metal complex activated tubing and PAA, metal complex activated polyurethane tubing were immersed in 5 mL of 10 mM metal complex solution from Example 1A. All the tubing was fully covered with the metal complex solution and placed on a rotary mixer for 30 minutes at 20-25° C. The metal polymer solution was then aspirated and excess drained onto paper towel.

Solutions of heparin (Sigma/SRE0027-100KU) or dalteparin (Sigma/Code D0070000) were diluted to 50 mg/mL with ddH$_2$O. Stock heparin or dalteparin solutions were diluted to 1 mg/mL in 10 mM MES (Sigma/M2933-500) pH5 buffer. Twenty segments of 0.5 cm polyurethane tubing coated with metal complex, PAA polymer and metal complex polymer were immersed in 5 mL of 1 mg/mL heparin or dalteparin solution. Again all the tubing was completely covered with the heparin solution and agitated with a rotary mixer for 30 minutes at 20-25° C. The heparin or dalteparin solution was then removed from the container and excess drained onto paper towel. The treated tubing was dried for 15 minutes at 20-25° C. and then for a further for 15 minutes at 37° C. The treated tubing was stored in desiccant cabinet overnight at 20-25° C. and then stored the tubing in a foil bag with desiccant at 4° C.

B. Biophen Heparin Anti-Xa Assay to Detect Functional Heparin or Dalteparin on Metal Complex Activated Polyurethane Tubing.

This assay determines the quantity of functional heparin by assessing the inhibition of the reaction of human antithrombin with the assay substrate. It is an indirect colorimetric assay. A kit was purchased from Hyphen BioMed (Cat No: 221010) and reagents used are listed previously in Example 3.

The 3×0.5 cm heparin coated tubing was cut to 0.25 cm sections and all pieces transferred to a 1.5 mL microfuge tube. Similarly the 3×0.5 cm dalteparin tubing were treated the same. The two types of coated tubings were washed with 1 mL of ddH$_2$O and the tube vortexed at medium speed for 10 second and then incubated 20 minutes at 20-25° C. The ddH$_2$O was aspirated. The heparin and dalteparin tubings were transferred to a 96 well plate (Greiner low bind PS) for biophen heparin assay.

All Biophen reagents (Biophen heparin Anti-Xa/Hyphen BioMed/Lot No: 52202) were pre-warmed to 37° C. prior to commencing assay. Diluted R1 (1:4) in R4 buffer before use. Diluted R2 (1:4) in R4 buffer before use. Heparin solutions were diluted to 0.1, 0.075, 0.05 and 0.025 IU/mL in R4 buffer. The 40 µL of diluted heparin was added to well as per template and 40 µL of R4 buffer was added to all tubing wells. 40 µL of diluted R1 was added to all wells. The plate was incubated for 2 minutes on a heated microplate shaker set at 37° C. with plate speed ~600 rpm. Diluted R2 was added to all wells. The plate was incubated for 2 minutes on a heated microplate shaker set at 37° C. with a mixing speed of ~600 rpm. Diluted R3 was added to all wells and incubated for 2 minutes at 37° C. on microplate shaker at ~600 rpm. The reaction was stopped with addition of 80 µL of stop solution. 200 µL of assay solution was transferred to a new Low Bind transparent plate for reading absorbance 405 nm using Tecan M200PRO.

Figure 6:
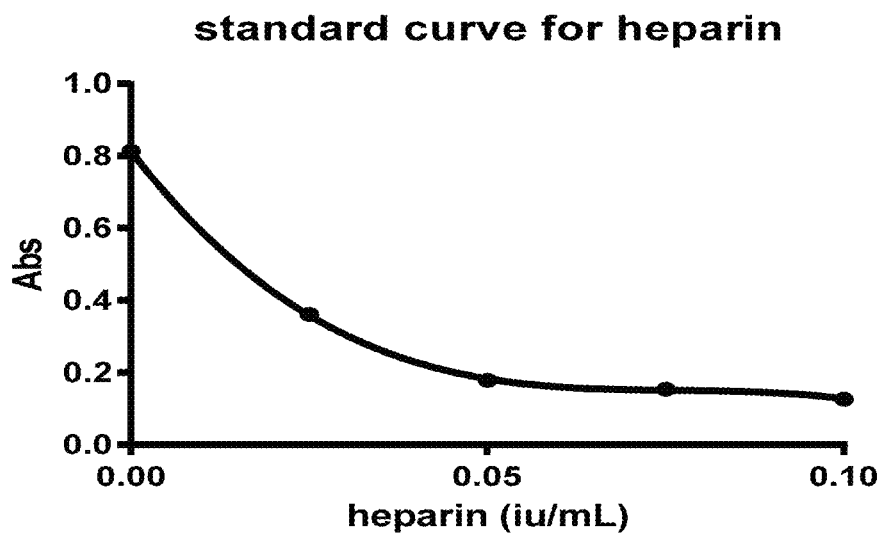
FIG. 6 is a graphical representation of a heparin standard curve from assays using polyurethane.
Figure 7:
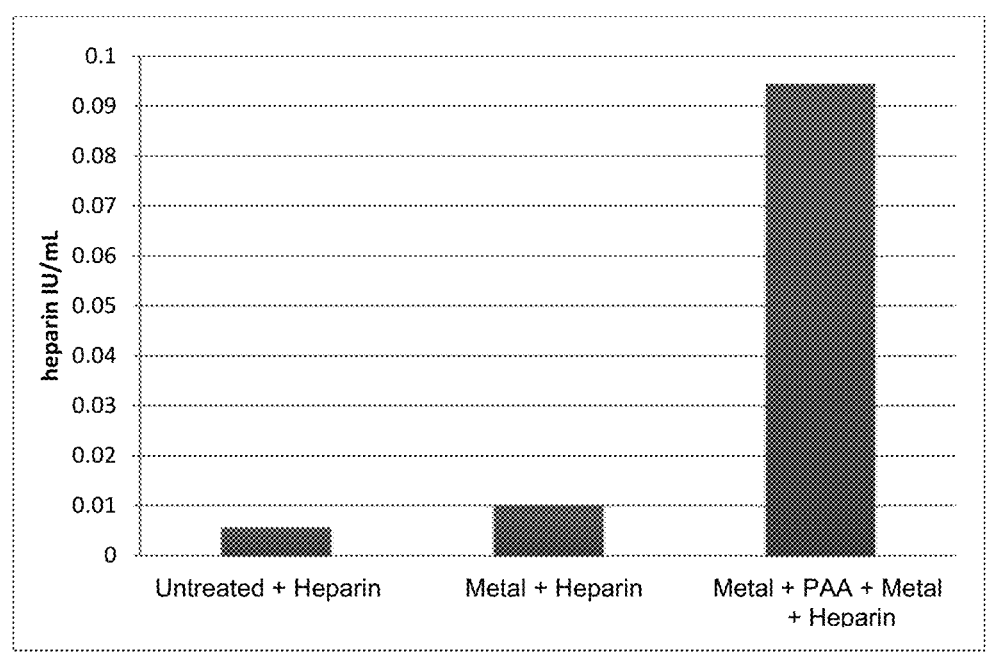
FIG. 7 is a graphical representation of the results of a competitive colorimetric assay for a functional heparin coated onto metal coordination complex activated polyurethane.

The functional standard curve for heparin is shown in FIG. 6. The functional heparin tubing assay data is shown in FIG. 7. The functional assay data shows comparable functionality of heparin bound to metal complex activated with multilayer metal, PAA and metal complex coated polyurethane tubing. The multilayer coating bound more heparin in total than a single layer metal complex coated polyurethane tubing. As a control, the untreated polyurethane tubing showed low activity in the biophen heparin anti-Xa assay.

Figure 8:
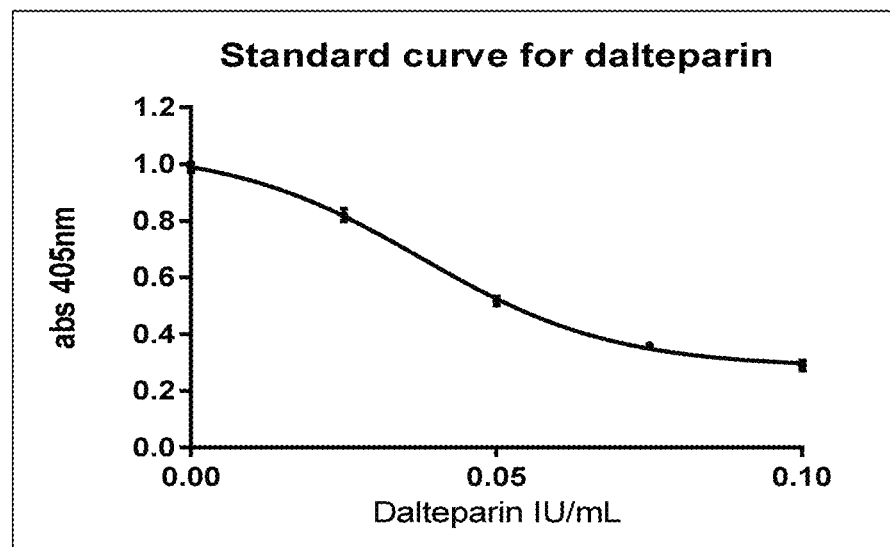
FIG. 8 is a graphical representation of a dalteparin standard curve from assays using polyurethane.
Figure 9:
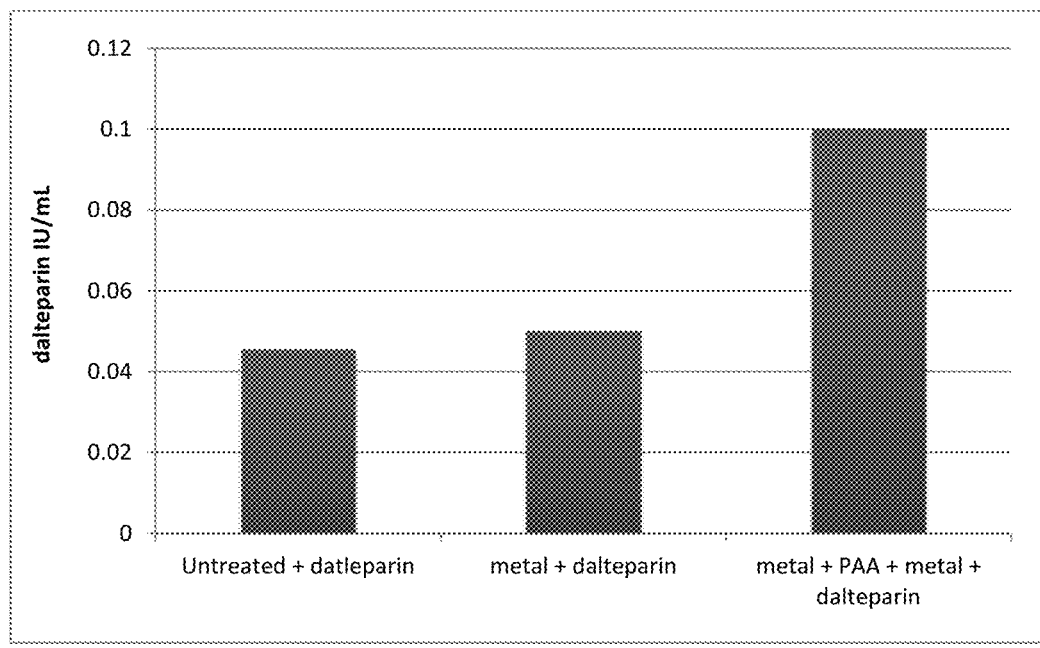
FIG. 9 is a graphical representation of the results of a competitive colorimetric assay for a functional dalteparin coated onto metal coordination complex activated polyurethane.

The functional standard curve for dalteparin is shown in FIG. 8. The functional dalteparin tubing assay data is shown in FIG. 9. The dalteparin tubing assay data for the three samples show the same pattern as the heparin tubing. The dalteparin multilayer tubing was loaded with more than 0.1 IU/mL and so was outside the dynamic range of the assay.

Example 5: Heparin and Dalteparin Bound to Oligomeric Metal Complex Coatings on Polypropylene A. Preparation of Two-Step Metal Complex Coatings on Polypropylene Plate.

Polypropylene (PP) plates were purchased from Greiner Bio-one Cat #650201 (Lot: 11511155) and coated are described in Example 4. In brief, the two step metal complex coating was done using 50 µL of a 5 mM solution of each metal complex per well of a PP plate. Subsequently, the wells were coated with 0.1% (wt/vol) polyacrylic acid (PAA) and then more metal complex solution was added, as described previously. Finally, heparin (Sigma/SRE0027-100KU) and dalteparin (Sigma/Code D0070000) were added and the coated plates dried as before.

B. Biophen Heparin Anti-Xa Assay to Detect Functional Heparin or Dalteparin on Metal Complex Activated Polypropylene.

Figure 10:
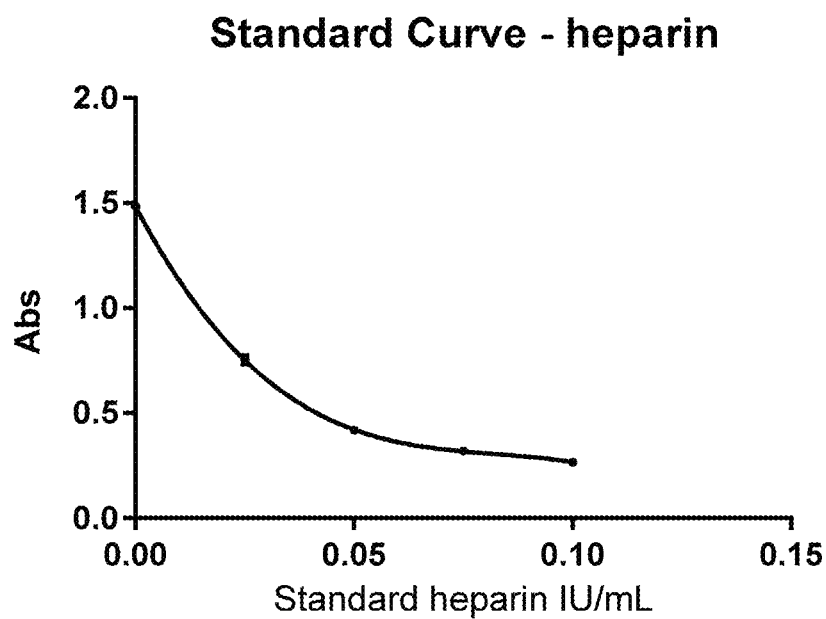
FIG. 10 is a graphical representation of a heparin standard curve from assays using polypropylene.
Figure 11:
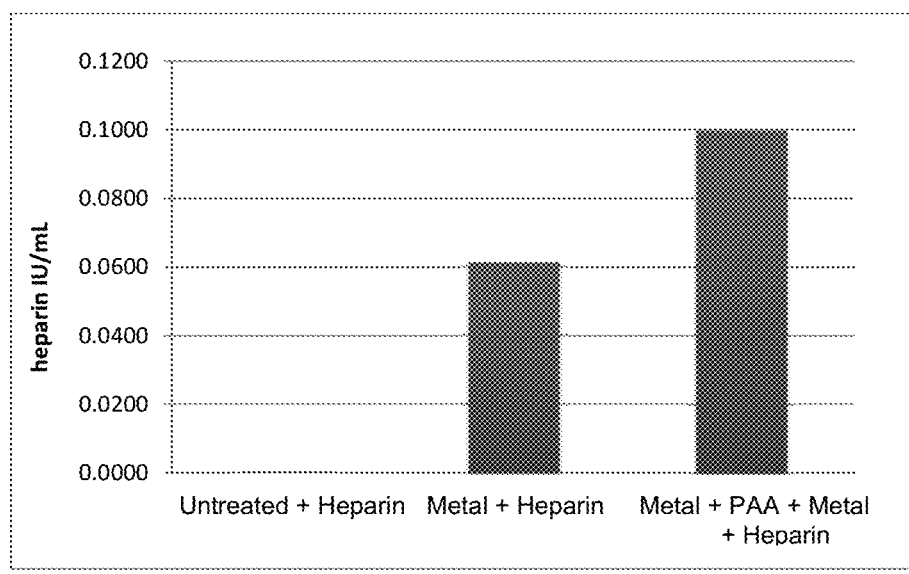
FIG. 11 is a graphical representation of the results of a competitive colorimetric assay for a functional heparin coated onto metal coordination complex activated polypropylene.

This assay is performed as described previously for Examples 3 and 4. The heparin standard curve is shown in FIG. 10. The results confirm the functionality of heparin bound to the metal complex activated polypropylene plate is shown in FIG. 11. As a control, the untreated PP wells have no detectable bound heparin demonstrated by the lack of inhibition of human anti-thrombin in the biophen assay.

Figure 12:
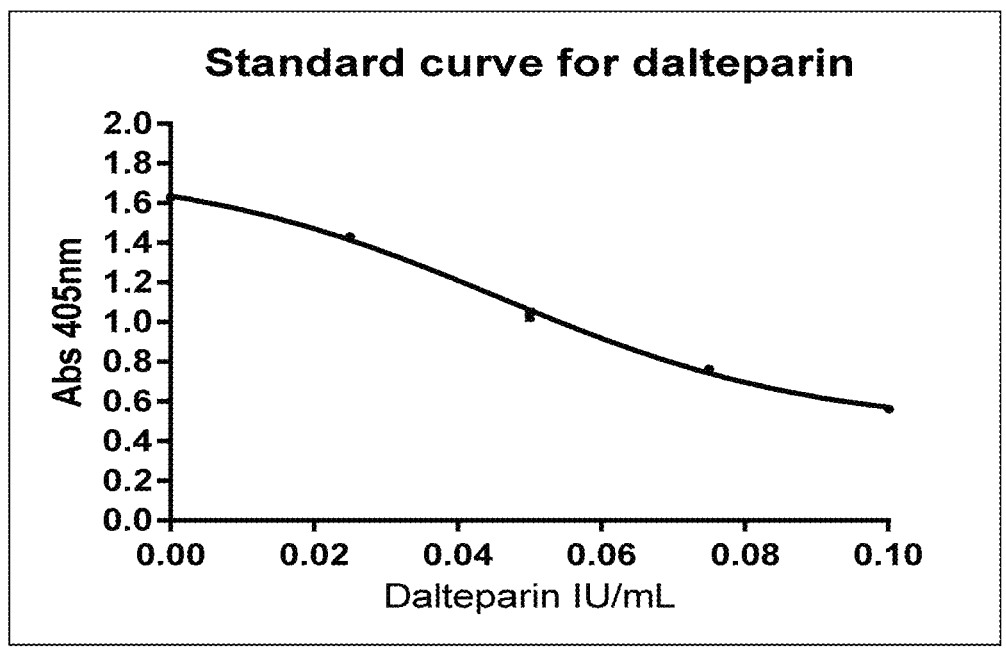
FIG. 12 is a graphical representation of a dalteparin standard curve from assays using polypropylene.
Figure 13:
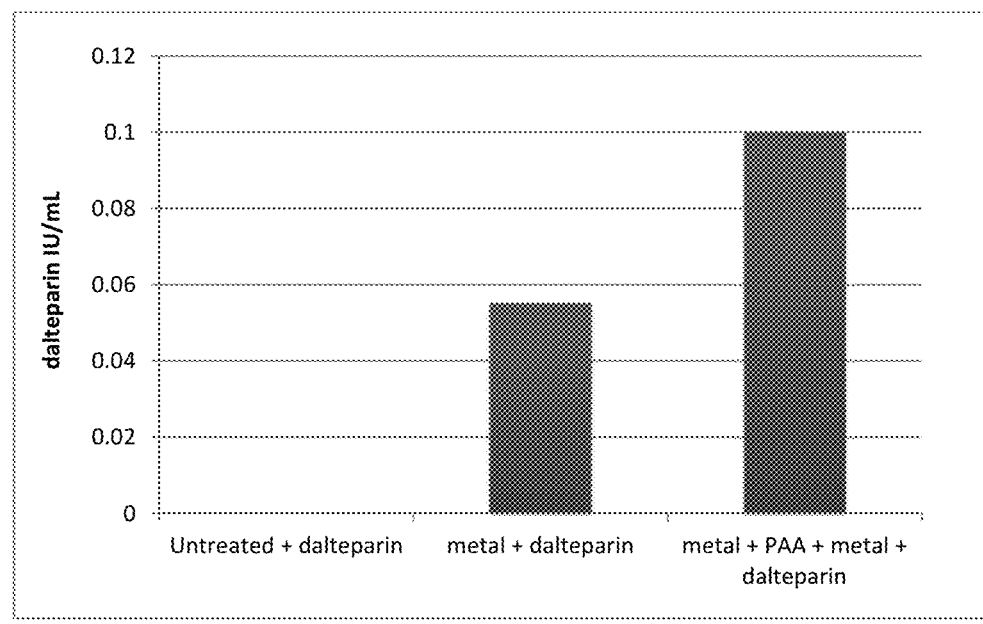
FIG. 13 is a graphical representation of the results of a competitive colorimetric assay for a functional dalteparin coated onto metal coordination complex activated polypropylene.

The functional standard curve for dalteparin is shown in FIG. 12. The dalteparin functionality assay data showed dalteparin bound to the metal complex activated polypropylene plate. As for the polyurethane tubing the polypropylene wells had bound more than 0.1 IU/mL of dalteparin. The functional dalteparin tubing assay data is shown in FIG. 13.

Example 6: Heparin and Mouse IgG Bound to Oligomeric Metal Complex Coated Polyurethane A. Preparation of Two-Step Metal Complex Coatings on Polyurethane Tubing.

In the manner as previously described in Example 4, oligomeric metal complexes were coated onto polyurethane tubing.

B. Binding Heparin and Mouse IgG to Activated Polyurethane Tubing.

Heparin (Sigma/SRE0027-100KU) was diluted to 50 mg/mL with $ddH_2O$. Mouse IgG (Lampire Biological Laboratories, Cat No: T404304) was supplied at 10 mg/ml. Stock heparin and Mouse IgG solutions were diluted to: 1 mg/mL of heparin only, 0.5 mg/mL of heparin+0.5 mg/mL of Mouse IgG, and 1 mg/mL of Mouse IgG only. Activated segments of polyurethane tubing (0.5 cm) were immersed in the three different solutions and agitated with a rotary mixer for 60 minutes at 20-25° C. The heparin, heparin+mouse IgG, mouse IgG solutions were then removed from the tubes and excess drained onto paper towel. The treated tubing was dried for 15 minutes at 20-25° C. and then for a further for 15 minutes at 37° C. The treated polyurethane tubings were stored in a desiccant cabinet overnight at 20-25° C. and relative humidity 22%, and then stored in a foil bag with desiccant for storage at 4° C.

C. Biophen Heparin Anti-Xa Assay on Coated Polyurethane Tubing.

Figure 14:
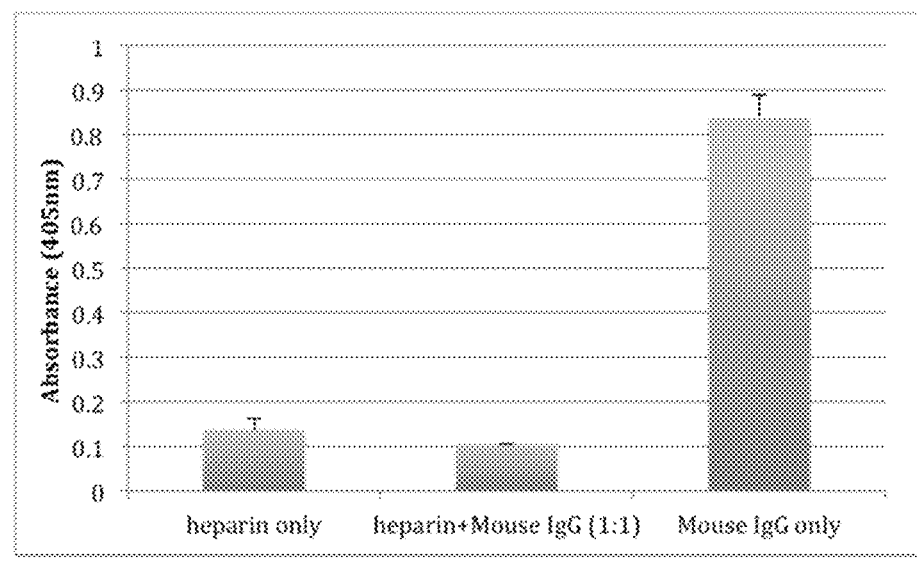
FIG. 14 is a graphical representation of the results of a functional assay showing activity for heparin and heparin+mouse IgG on metal complex activated polyurethane tubing.

As described in Example 4B, this assay determines the quantity of functional heparin by assessing the inhibition of the reaction of human anti-thrombin with the assay substrate. As shown in FIG. 14, the functional assay data shows activity for both heparin bound as well as heparin+mouse IgG bound polyurethane. So metal complex activated polyurethane can simultaneously bind both heparin and mouse IgG. As expected, the control having just mouse IgG coated onto polyurethane did not show any heparin activity.

D. Goat Anti Mouse IgG-RPE Assay on Coated Polyurethane Tubing.

Mouse IgG loading assay on metal complex activated polyurethane tubing was performed according to the procedure below. Allow all reagents to come to room temperature. Diluted the stock 0.5 mg/mL of Goat anti mouse IgG-RPE (Jackson, Code: 115-116-072, Lot: 126036) to 5 µg/mL in 1% BSA, 50 mM TBS, 0.05% Tween 20, 0.05% ProClin 300, pH8. Heparin, heparin+mouse IgG, and mouse IgG coated polyurethane tubing were produced as above. The coated tubings were added to a 96 well plate (Greiner white U bottom low bind PS) for Goat anti-Mouse IgG-RPE assay. Goat anti-Mouse IgG-RPE solution (200⁴) was added to the wells, and the plate incubated for 60 minutes on a plate shaker at 20-25° C. The polyurethane tubing was washed 3×200⁴ using Wash Buffer (50 mM TBS, 0.05% Tween20, 0.05% ProClin 300, pH8). Wash Buffer (100⁴) was added into all wells and the plate was read on a Tecan M200PRO (Setting Excitation wavelength: 546 nm, Emission wavelength: 575 nm).

Figure 15:
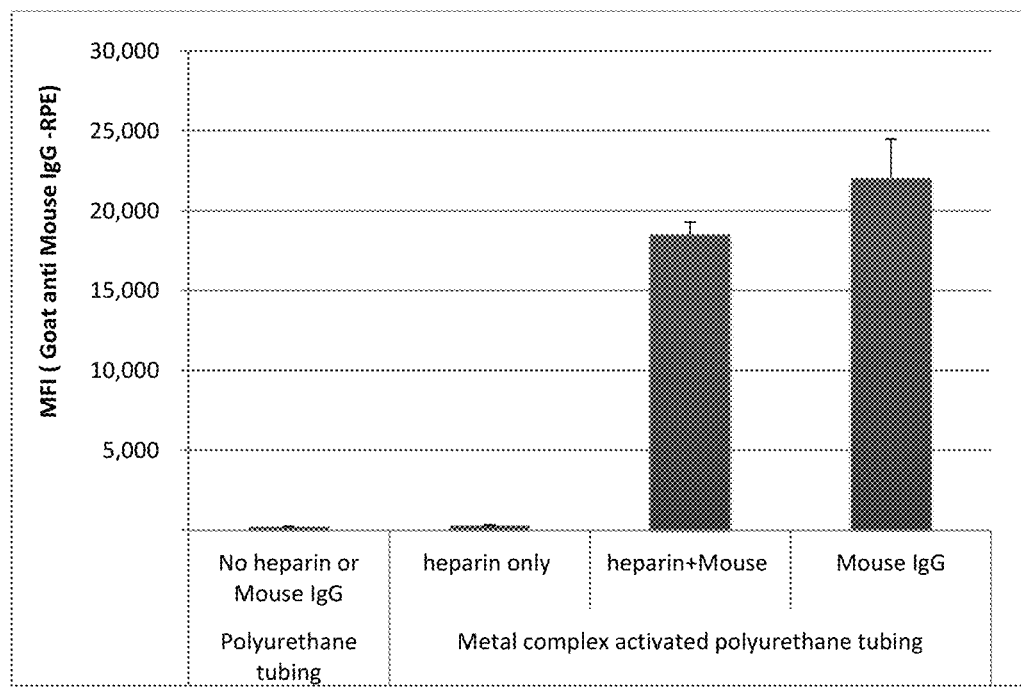
FIG. 15 is a graphical representation of the results of an anti Mouse IgG-RPE loading assay with heparin+mouse IgG and mouse IgG on metal complex activated polyurethane tubing.

The goat anti mouse IgG-RPE assay showed strong binding for both heparin+mouse IgG and mouse IgG coated polyurethane but not heparin coated polyurethane. The loading assay data is summarised in FIG. 15.

Example 8—Prophetic Example Varying Strength of Binding to Metal Complex of Heparin Versus a Low Molecular Weight Heparin (Dalteparin)

The strength of individual coordination bonds between the metal complex and a functional heparin ligand can be further manipulated by variations in temperature and time. Incubation at higher temperatures such as, for example, 40° C., 60° C., 100° C., can further strengthen the coordinate bonds to heparin, thereby increasing its stability on a substrate. Factoring in the other variables such as density of coordination sites on the substrate, it is possible to control the overall stability of different heparin analogues to allow for release of dalteparin from the substrate while substantially maintaining the functional heparin bound to the substrate.

To exemplify this, a series of parallel experiments can be carried out largely in the manner of those previously described, including Examples 4 and 5, but with a higher incubation time and/or temperature during the exposure of heparin to the metal complex. The temperature will be varied by increasing it in increments of 10° C., from room temperature, up to a maximum of about 150° C. during heparin binding. Similar experiments will be carried out varying the time by extending incubation time of heparin with the metal complex by 1 hour increments up to a 24 hour or 48 hour upper limit. A further set of similar experiments will be performed increasing the incubation temperature and also extending the incubation time in increments as already described to find an optimum for stabilising heparin binding.

Functionality can be measured with assays as described in the previous examples. Release of dalteparin will be initiated by incubation in the appropriate buffer system under conditions consistent with the milieu in which the device (i.e. the substrate) will be implanted. For example, release may be initiated by immersion in PBS incubated at 37° C. Release of functional heparin into the buffer can be evaluated as per example 4 and quantified by dilution of eluate until within the dynamic range of the assay. Similarly heparin that remains bound to the device can be detected by inclusion of a portion of wash of the device in the assay described in example 4. Alternatively the presence of functional heparin retained on the surface can be assessed using a thrombus formation inhibition assay, plasma recalcification time or other published method. This will demonstrate the uniformity and function of retained heparin and LMWH.

The invention claimed is:

1. A substrate having a hemocompatible coating comprising:
    (a) an oligomeric metal ion coordination complex comprising bridging ligands having a dative bond forming atom selected from nitrogen, oxygen, and sulfur, each datively bonded to at least two central metal ions, the oligomeric metal ion coordination complex bonded directly to a surface of the substrate through one or more coordinate bonds formed between the metal ions of the oligomeric metal ion coordination complex and the substrate surface; and
    (b) a functional heparin layer bonded directly to metal ions of the oligomeric metal ion coordination complex through one or more coordinate bonds;

wherein, the oligomeric metal ion coordination complex is a separate layer from and is of a different character to the surface of the substrate, but is bonded to the surface of the substrate.

2. The substrate of claim 1 wherein the metal of the metal coordination complex is selected from the group consisting of chromium, ruthenium, iron, cobalt, aluminum, zirconium, and rhodium.

3. The substrate of claim 2, wherein the chromium ion is a chromium (III) ion.

4. The substrate of claim 1, wherein the metal coordination complex is an oxo-bridged chromium (III) complex.

5. The substrate of claim 1 wherein the substrate is selected from the group consisting of a medical device and a nanoparticle.

6. The substrate of claim 1 wherein the substrate surface is formed from a material selected from the group consisting of a metal, a metalloid, a metal alloy, a metalloid alloy and a polymer.

7. The substrate of claim 1 wherein the substrate surface comprises a material having electron-donating groups selected from oxo groups, oxides, carboxylic acid-functionalized, amide functionalized, amine functionalized, hydroxyl functionalized, and aldehyde functionalized.

8. The substrate of claim 1 wherein the hemocompatible coating further comprises a co-bonding agent bonded directly to the metal coordination complex.

9. The substrate of claim 8 wherein the co-bonding agent is selected from the group consisting of a polysaccharide, a biological or synthetic polymer presenting electron donating groups, an antibody, a protein, a peptide, a labelling agent and a small molecule therapeutic.

10. The substrate of claim 1 wherein the functional heparin layer comprises a plurality of individual functional heparin molecules, each of which are bonded to the oligomeric metal ion coordination complex through multiple coordinate bonds.

11. The substrate of claim 1, wherein the oligomeric metal ion coordination complex is bonded directly to a surface of the substrate through one or more coordinate bonds formed between the metal ions of the oligomeric metal ion coordination complex and one or more electron-donating groups on the substrate surface.

12. The substrate of claim 1, wherein the functional heparin layer is bonded to the oligomeric metal ion coordination complex on a face thereof substantially opposite a face which is bonded to the substrate surface.

13. A method of forming a hemocompatible coating on a substrate including the steps of:
(a) forming a metal coordination complex layer on a surface of the substrate, wherein the metal coordination complex layer comprises an oligomeric metal ion coordination complex comprising bridging ligands having a dative bond forming atom selected from nitrogen, oxygen, and sulfur, each datively bonded to at least two central metal ions, the oligomeric metal ion coordination complex bonded directly bonded to a surface of the substrate through one or more coordinate bonds formed between the metal ions of the oligomeric metal ion coordination complex and the substrate surface;
(b) coating the metal coordination complex with a functional heparin such that the functional heparin bonds directly to metal ions of the oligomeric metal ion coordination complex through one or more coordinate bonds,
to thereby form the hemocompatible coating on the substrate.

14. The method of claim 13 further comprising the step of coating the metal coordination complex with a co-bonding agent prior to or at the same time as the coating with the functional heparin.

15. The method of claim 13 further comprising, prior to the forming of the metal coordination complex layer on the surface of the substrate, the step of contacting the substrate with a polymer to modify the surface of the substrate to present a greater density of electron donating groups.

16. The method of claim 13 including the step of varying the temperature and/or incubation time during the coating of the metal coordination complex with the functional heparin.

17. A method of reducing the incidence of thrombosis in a target area of a patient including implanting the substrate of claim 1 within the target area.

18. The method of claim 17 wherein the substrate is a medical device.

* * * * *